United States Patent [19]

Siegrist et al.

[11] Patent Number: 5,856,578
[45] Date of Patent: Jan. 5, 1999

[54] PROCESS FOR THE PREPARATION OF UNSATURATED AMINO COMPOUNDS

[75] Inventors: Urs Siegrist, Eiken; Peter Baumeister, Flüh, both of Switzerland

[73] Assignee: Norvartis Corporation, Summit, N.J.

[21] Appl. No.: 737,848

[22] PCT Filed: May 16, 1995

[86] PCT No.: PCT/EP95/01847

§ 371 Date: Nov. 25, 1996

§ 102(e) Date: Nov. 25, 1996

[87] PCT Pub. No.: WO95/32941

PCT Pub. Date: Dec. 7, 1995

[30] Foreign Application Priority Data

May 27, 1994 [SE] Sweden .................................. 1648/94

[51] Int. Cl.[6] .................................................. C07C 209/48
[52] U.S. Cl. ............................ 564/423; 560/23; 560/90; 558/411; 558/416; 564/164
[58] Field of Search .................... 564/423, 164; 560/23, 90; 558/416, 411

[56] References Cited

U.S. PATENT DOCUMENTS

| 2,823,235 | 2/1958 | Graham et al. . |
| 3,666,813 | 5/1972 | Hindin et al. . |
| 3,867,280 | 2/1975 | Paynter et al. . |
| 3,975,444 | 8/1976 | Kovar et al. . |
| 4,051,177 | 9/1977 | Braden et al. . |
| 4,212,827 | 7/1980 | Seagraves . |
| 4,532,351 | 7/1985 | Barnett et al. ........................... 564/415 |
| 4,661,643 | 4/1987 | Bartley .................................... 568/678 |
| 5,068,436 | 11/1991 | May . |
| 5,235,106 | 8/1993 | Didillon et al. . |

FOREIGN PATENT DOCUMENTS

| 494568 | 7/1992 | European Pat. Off. . |
| 2257332 | 8/1975 | France . |
| 2042368 | 4/1971 | Germany . |
| 3228420 | 2/1984 | Germany . |
| 243332 | 9/1944 | Switzerland . |
| 594816 | 11/1947 | United Kingdom . |
| 1282000 | 7/1972 | United Kingdom . |
| WO9109023 | 6/1991 | WIPO . |

OTHER PUBLICATIONS

Chem. Abstr. vol. 97, No. 23, 6 Dec. 1982, No. 197995k.
Coq et al., J. Mol. Catal., 71 (1992), 317–333.

*Primary Examiner*—Brian M. Burn
*Attorney, Agent, or Firm*—Gabriel Lopez

[57] ABSTRACT

The present invention relates to a process for the preparation of aromatic amino compounds which are substituted by a least one group comprising at least one unsaturated carbon-carbon bond, by catalytic hydrogenation of corresponding aromatic nitro compounds in the presence of a modified noble metal catalyst, wherein the noble metal catalyst used is platinum modified with a metal selected from the group consisting of lead, mercury, bismuth, germanium, cadmium, arsenic, antimony, silver and gold, and to novel noble metal catalysts for use in this process.

33 Claims, No Drawings

PROCESS FOR THE PREPARATION OF UNSATURATED AMINO COMPOUNDS

Process for the preparation of unsaturated amino compounds.

The present invention relates to a novel process for the preparation of aromatic amino compounds which are substituted by at least one group which comprises at least one unsaturated carbon-carbon bond, in the presence of a modified noble metal catalyst, and to novel noble metal catalysts for use in this process.

It is known that nitrated aromatic compounds can be reduced to aromatic amines in the presence of noble metal catalysts. In the case of nitrated aromatic compounds substituted by groups which comprise at least one unsaturated carbon-carbon bond, however, the inadequate selectivity of the catalyst leads to unwanted hydrogenation of the unsaturated carbon-carbon bonds. The separation of these unwanted by-products is either impossible or can only be carried out at considerable expense.

In order to counter this problem it has been proposed, for example in DE-A-2 362 780, to use cobalt sulfide as catalyst. This catalyst has the grave disadvantage that, in the course of hydrogenation, sulfur-containing by-products are formed which reduce the quality of the product and severely limit the reusability of the solvents. In addition, highly volatile sulfur compounds are formed during the reaction, one example being hydrogen sulfide, whose leakage from the reactor, particularly in the case of large-scale industrial syntheses, leads to considerable safety problems.

From JP 82,120,553 it is known to prepare aromatic amines, which may be substituted by groups comprising unsaturated carbon-carbon bonds, by hydrogenating the corresponding nitro compounds in the presence of a palladium catalyst and in the presence of a carboxylic acid, such as dinitrobenzoic acid. Using this process to prepare 2-(3,5-diaminobenzoyloxy)ethyl methacrylate, the yield is only 85.5%, providing little satisfaction especially in the case of large-scale industrial application.

From FR-A-2257332 it is known that a catalytical composition comprising (a) a porous support, (b) platin, (c) mangan, (d) iridium and (e) at least one of the metals of group IV of the periodical classification which is selected from the elements germanium, tin and lead can be used to convert hydrocarbonates and particularly to dehydrogenate and hydrogenate hydrocarbonates.

It has been found that this aim can be achieved advantageously by using specially modified platinum catalysts. Counter to expectations, it has been found that, with these catalysts, nitroaromatic compounds can be reduced selectively to the corresponding amino compounds without at the same time hydrogenating the unsaturated carbon-carbon bond-containing side-chains of the nitroaromatic compound.

In accordance with the present invention it is therefore proposed to prepare aromatic amino compounds which are substituted by at least one group comprising at least one unsaturated carbon-carbon bond, by means of catalytic hydrogenation of corresponding aromatic nitro compounds in the presence of a modified noble metal catalyst, by using as noble metal catalyst platinum which is modified with a metal selected from the group consisting of lead, mercury, bismuth, germanium, cadmium, arsenic, antimony, silver and gold.

Some of the catalysts used in the process according to the invention are novel and others are known. DE-A 2 042 368 and J. Mol. Catal. 71,(1992) 317 describe the preparation and use of platinum catalysts, modified with tin, lead, germanium, aluminium, zinc, bismuth and silver, for the preparation of halogen-substituted aromatic amines.

It has surprisingly been found that, if compounds of iron, ruthenium, cobalt, copper or manganese are used as additional promoters for the lead-, mercury-, bismuth-, germanium-, cadmium-, arsenic-, antimony-, silver- and gold-modified platinum catalysts, the yields in the process according to the invention can be raised further. These catalysts are novel and are a further subject of the present invention.

The promoters can be either added directly to the reaction mixture as salts or deposited as insoluble compound on the surface of the catalyst in the course of its preparation or modification.

Preferred promoters which can be used in the catalysts are: $Fe^{2+}$, $Fe^{3+}$, $Ru^{3+}$, $Mn^{2+}$ and $Mn^{3+}$ as salts with the anions $Cl^-$, $Br^-$, $F^-$, $SO_4^{2-}$, $NO_3^-$, acetate, citrate, gluconate, lactate, oxalate, benzoate, naphthenate, tartrate and formate or in the form of an appropriate metal complex.

The promoter is preferably used in a quantity of from 0.001 to 10% by weight, based on the aromatic nitro compound employed, with the promoter used being, in particular, an iron salt, very preferably $FeCl_2 4H_2O$.

The use of compounds of iron and manganese as promoters for certain platinum catalysts which are able selectively to reduce aromatic nitro compounds to the corresponding amines in the presence of halogen is known, for example, from U.S. Pat. Nos. 4,212,824 and 2,823,235.

In addition to the promoters mentioned, the hydrogenation can be accelerated by using a co-promoter. Suitable co-promoters are, in general, ion pairs or salts which are soluble in organic solvents, preferably ionophores which are known from electrochemistry, and in particular as cation $(C_1-C_6alkyl)_4N^+$ or

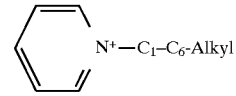

and as anion $Cl^-$, $Br^-$, $F^-$, $BF_4^-$, $PF_6^{31}$, $NO_3^-$, $F_3CSO_3^-$, $BPh_4^-$, $PhCOO^-$,

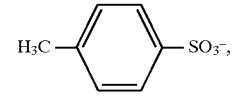

$CH_3SO_3^-$ and $F_3COO^-$. The use of these co-promoters is particularly preferred in the process according to the invention. Very particular preference is given to the use of co-promoters consisting of quaternary ammonium bases, especially tetramethylammonium chloride. The co-promoters are preferably used in a quantity of from 0.001 to 10% by weight, based on the aromatic nitro compound employed.

In the process according to the invention, the metal modifying the platinum catalyst is preferably lead, in particular in the form of lead acetate, lead nitrate, lead chloride and lead tetraalkyls, for example lead tetraethyl.

The noble metal catalyst is used in particular in a quantity of from 0.1 to 5% by weight, based on the aromatic nitro compound employed, with the weight ratio of platinum to the modifying metal being from 1:0.001 to 1:1, preferably from 1:0.1 to 1:0.5.

It is preferred to use a noble metal catalyst which contains from 1 to 10% by weight of platinum. The platinum which can be employed for the modification can be used in the form of platinum black, platinum oxide or, preferably, in metallic or oxidized form applied to a support. Particularly suitable supports are active charcoal, silicic acid, silica gel, alumina, calcium carbonate, calcium phosphate, calcium sulfate, barium sulfate, titanium oxide, magnesium oxide, iron oxide, lead oxide, lead sulfate or lead carbonate, particular preference being given to active charcoal, alumina or calcium carbonate. Platinum applied to an abovementioned support material is commercially available or can be prepared by methods which are familiar to those skilled in the art, as are described, for example, in DE-A-2 042 368.

The process according to the invention is carried out at a pressure of from 1 to 100 bar and at a temperature of from +20° to +160° C., preferably at a pressure of from 20 to 40 bar and at a temperature of from +100° to +140° C.

The noncritical choice of the solvent is a particular advantage of the process according to the invention. It is possible to employ solvents of high solvency which are not sufficiently inert in the presence of unmodified platinum catalysts, examples of these solvents being ketones. Preferred solvents are water, alcohols such as methanol, ethanol, n-propanol, isopropanol, n-butanol, the isomeric butanols and cyclohexanol, ethers, esters and ketones, for example diethyl ether, methyl tert-butyl ether, tetrahydrofuran, dioxane, dimethoxyethane, ethyl acetate, butyl acetate, butyrolactone, acetone, methyl ethyl ketone, methyl isobutyl ketone or cyclohexanone, carboxylic acids such as acetic acid and propionic acid, dipolar aprotic solvents such as dimethylformamide, N-methylpyrrolidone, dimethylacetamide, sulfolane, dimethyl sulfoxide or acetonitrile, apolar solvents such as toluene or xylene, chlorinated aromatic hydrocarbons and also methylene chloride, $C_3$–$C_7$ alkanes or cyclohexane.

These solvents can be employed in pure form or as mixtures. In particularly preferred embodiments of the process according to the invention the solvents used are tetrahydrofuran, dimethoxyethane, methyl ethyl ketone, acetone and also cyclohexanone in pure form or as mixtures with alcohols and/or $C_1$–$C_4$ carboxylic acids.

The unsaturated carbon-carbon bonds according to the present invention comprise alkene, alkyne and allene bonds.

The aromatic nitro compounds can be substituted by any groups which behave inertly in the process according to the invention.

The terms aromatic nitro compounds and amino compounds in the context of the present invention refer to those systems which obey Hüickel's 4n+2 electron rule, for example aromatic hydrocarbons such as benzenes, polycyclic hydrocarbons (including those which are partially hydrogenated, such as tetralin), biphenyls, cyclopentadienyl anion and cycloheptatrienyl anion, heteroaromatic compounds such as pyridines, pyrroles, azoles, diazines, triazines, triazoles, furans, thiophenes and oxazoles, condensed aromatic compounds such as indoles, quinolines, isoquinolines, carbazoles, purines, phthalazines, benzotriazoles, benzofurans, cinnolines, quinazoles, acridines and benzothiophenes.

The aromatic nitro compounds may comprise one or more nitro groups.

The process according to the invention is particularly suitable for the preparation of aromatic amino compounds which, as described for example in U.S.-Pat. No. 3 975 444, can be used as terminal blocking groups for heterocyclic oligomers, or, as disclosed for example in WO 91/09023, are used as intermediates in the preparation of cardiovascular medicaments.

With very particular preference the process according to the invention is suitable for the preparation of aromatic amino compounds which are used as intermediates in the preparation of herbicidal 3-aryluracil derivatives as described, for example, in U.S. Pat. No. 5 183 492. These aromatic nitro compounds conform to the formula I:

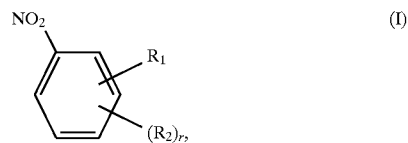

in which $R_1$ is a group comprising at least one unsaturated carbon-carbon bond; r is 1, 2, 3, or 4;

$R_2$ is hydrogen, $C_1$–$C_{12}$alkyl, $C_1$–$C_{12}$haloalkyl, $C_1$–$C_{12}$hydroxyalkyl, $C_1$–$C_6$cyanoalkyl, $C_3$–$C_8$cycloalkyl, $C_6$–$C_{16}$aryl, $C_7$–$C_{16}$aralkyl, $C_3$–$C_{16}$heterocycloalkyl, $C_3$–$C_{16}$heteroaryl, $C_4$–$C_{16}$heteroarylalkyl, halogen, cyano, $COR_3$, $X_{X1}R_4$, —$COR_8$,

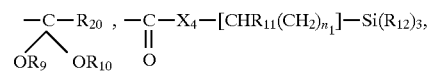

—$N(R_{13})$—$SO_2$—$R_{14}$,

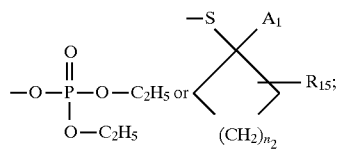

$A_1$ is cyano or —$COR_{16}$;

$R_3$ is halogen, $X_2$—$R_5$, amino, $C_1$–$C_4$alkylamino, di-$C_1$–$C_4$alkylamino, $C_2$–$C_4$haloalkylamino, di-$C_2$–$C_4$-haloalkylamino, $C_1$–$C_4$alkoxyalkylamino, di-$C_1$–$C_4$-alkoxyalkylamino, $C_2$–$C_4$alkenylamino, diallylamino, —N-pyrrolidino, —N-piperidino, —N-morpholino, —N-thiomorpholino, —N-piperidazino;

$R_4$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl which is unsubstituted or is substituted on the phenyl ring by up to three identical or different substituents consisting of halogen, $C_1$–$C_4$alkyl, halo-$C_1$–$C_4$alkyl, halo-$C_1$–$C_4$alkoxy or $C_1$–$C_4$alkoxy; or is furanoyl, thienyl; or is $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_2$–$C_8$alkenyloxycarbonyl, $C_3$–$C_8$alkynyloxycarbonyl, $C_1$–$C_8$alkylthiocarbonyl, $C_2$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$-alkylaminocarbonyl; or is phenylaminocarbonyl which is unsubstituted or is substituted on the phenyl by up to three identical or different substituents consisting of halogen, $C_1$–$C_4$alkyl, halo-$C_1$–$C_4$alkyl, halo-$C_1$–$C_4$alkoxy or $C_1$–$C_4$alkoxy or is substituted once by cyano, or is dioxolan-2-yl which is unsubstituted or is substituted by one or two $C_1$–$C_4$alkyl groups; or is dioxan-2-yl, which is unsubstituted or is substituted by one or two $C_1$–$C_4$alkyl groups, or is $C_1$–$C_4$alkyl which is substituted by cyano, carboxyl or $C_1$–$C_8$alkylthio-$C_1$–$C_8$alkaoxycarbonyl;

$R_5$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$alkylthio-$C_1$–$C_4$alkyl, di-$C_1$-$C_4$alkylamino-$C_1$-$C_4$alkyl, cyano-$C_1$-$C_8$alkyl, $C_2$-$C_8$alkenyl, halo-$C_2$-$C_8$alkenyl, $C_3$-$C_8$alkynyl, $C_3$-$C_7$cycloalkyl, $C_3$-$C_7$cycloalkyl-$C_1$-$C_4$alkyl, halo-$C_3$-$C_7$cycloalkyl or benzyl which is unsubstituted or is substituted on the phenyl ring by up to three identical or different substituents consisting of halogen, $C_1$-$C_4$alkyl, halo-$C_1$-$C_4$alkyl, halo-$C_1$-$C_4$alkoxy or $C_1$-$C_4$alkoxy, or is an alkali metal, alkaline earth metal or ammonium ion, or is the group —[$CHR_6(CH_2)_{n_3}$]—$COOR_7$;

$R_6$ is hydrogen or $C_1$-$C_4$alkyl;

$R_7$ is hydrogen, $C_1$-$C_6$alkyl, $C_2$-$C_8$alkenyl, $C_3$-$C_8$alkynyl, $C_1$-$C_8$alkoxy-$C_2$-$C_8$alkyl, $C_1$-$C_8$alkylthio-$C_1$-$C_8$alkyl or $C_3$-$C_7$cycloalkyl;

$R_8$ and $R_{20}$ independently of one another are hydrogen, $C_1$-$C_4$alkyl, halo-$C_1$-$C_4$alkyl or $C_1$-$C_4$alkoxy-$C_1$-$C_4$alkyl;

$R_9$ and $R_{10}$ independently of one another are each $C_1$-$C_4$alkyl, $C_2$-$C_4$haloalkyl or $C_2$-$C_8$-alkoxyalkyl, or $R_9$ and $R_{10}$ together are an ethano, propano or a cyclohexane-1,2-diyl bridge, these groups either being unsubstituted or being able to be substituted by one or two $C_1$-$C_4$alkyl, $C_1$-$C_4$haloalkyl or $C_1$-$C_4$hydroxyalkyl groups;

$R_{11}$ is hydrogen, $C_1$-$C_5$alkyl or $C_3$-$C_7$alkenyl;

$R_{12}$ is $C_1$-$C_8$alkyl;

$R_{13}$ is hydrogen, $C_1$-$C_5$alkyl, benzyl, halo-$C_1$-$C_4$alkyl, $C_2$-$C_8$alkenyl or $C_3$-$C_8$alkynyl;

$R_{14}$ is $C_1$-$C_6$alkyl, halo-$C_1$-$C_5$alkyl or di-$C_1$-$C_4$alkylamino;

$R_{15}$ is hydrogen, fluorine, chlorine, bromine, $C_1$-$C_4$alkyl or trifluoromethyl;

$R_{16}$ is $X_3$—$R_{17}$, amino, $C_1$-$C_4$alkylamino, di-$C_1$-$C_4$alkylamino, $C_2$-$C_4$haloalkylamino, di-$C_2$-$C_4$haloalkylamino, $C_1$-$C_4$alkoxyalkylamino, di-$C_1$-$C_4$alkoxyalkylamino, $C_2$-$C_4$alkenylamino, diallylamino, —N-pyrrolidino, —N-piperidino, —N-morpholino, —N-thiomorpholino, —N-piperidazino, the group —O—N=C—($CH_3$)—$CH_3$, —O—$CH_2$—$CH_2$—O—N=C($CH_3$)—$CH_3$ or the group —N($OR_{24}$)—$R_{22}$;

$R_{17}$ is hydrogen, $C_1$-$C_{10}$alkyl, $C_1$-$C_4$alkoxy-$C_1$-$C_4$alkyl, halo-$C_1$-$C_8$alkyl, $C_1$-$C_{10}$-alkylthio-$C_1$-$C_4$alkyl, di-$C_1$-$C_4$alkylamino-$C_1$-$C_4$alkyl, cyano-$C_1$-$C_8$alkyl, $C_2$-$C_8$alkenyl, halo-$C_2$-$C_8$alkenyl, $C_3$-$C_8$alkynyl, $C_3$-$C_7$cycloalkyl, $C_3$-$C_7$cycloalkyl-$C_1$-$C_4$alkyl, halo-$C_3$-$C_7$cycloalkyl or benzyl which is unsubstituted or is substituted on the phenyl ring by up to three identical or different substituents consisting of halogen, $C_1$-$C_4$alkyl, halo-$C_1$-$C_4$alkyl, halo-$C_1$-$C_4$alkoxy or $C_1$-$C_4$alkoxy, or is an alkali metal, alkaline earth metal or ammonium ion, or is the group —[$CHR_{25}$—$(CH_2)_m$]—$COOR_{26}$ or the group [$CHR_{27}$—$(CH_2)_t$ —$Si(R_{23})_3$];

$R_{22}$ is hydrogen or $C_1$-$C_4$alkyl;

$R_{23}$ is $C_1$-$C_4$alkyl, halo-$C_1$-$C_4$alkyl or $C_1$-$C_4$alkoxy-$C_1$-$C_4$alkyl;

$R_{24}$ and $R_{25}$ independently of one another are hydrogen or $C_1$-$C_4$alkyl;

$R_{26}$ independently at each occurrence is hydrogen, $C_1$-$C_6$alkyl, $C_2$-$C_8$alkenyl, $C_3$-$C_8$alkynyl, $C_1$-$C_8$alkoxy-$C_2$-$C_8$alkyl, $C_1$-$C_8$alkylthio-$C_1$-$C_8$alkyl or $C_3$-$C_7$cycloalkyl;

$R_{27}$ is hydrogen or $C_1$-$C_4$alkyl;

m is 0, 1, 2, 3 or 4;

t is 0, 1, 2, 3 or 4 $n_1$, $n_2$ and $n_3$ independently of one another are 0, 1, 2, 3 or 4; and $X_1$, $X_2$, $X_3$ and $X_4$ independently of one another are oxygen or sulfur.

In the compound of the formula I r is preferably 1 or 2. In addition, emphasis should be placed on those compounds of the formula I in which the unsaturated carbon-carbon bond of substituent $R_1$ is part of an ester group.

A further preferred subgroup of compounds of the formula I is that in which $R_2$ is hydrogen, halogen, $C_1$-$C_6$alkyl, $C_1$-$C_6$alkoxy, $C_1$-$C_6$haloalkoxy or cyano, with $R_2$ preferably being hydrogen, halogen, methyl, difluoromethoxy, trifluoromethoxy or cyano.

The process according to the invention is particularly suitable for the reaction of aromatic nitro compounds of the formula Ia

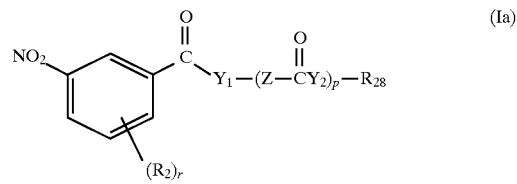

in which $R_2$ and r are as defined under formula I, and $R_{28}$ is $C_2$-$C_6$alkenyl, $C_3$-$C_6$alkynyl, $C_3$-$C_8$cycloalkenyl or $C_6$-$C_8$bicycloalkenyl;

$Y_1$ is oxygen, —NH—, the group

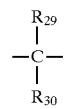

or the group

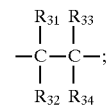

$R_{29}$ and $R_{30}$ independently of one another are hydrogen or $C_1$-$C_4$alkyl; or $R_{29}$ and $R_{30}$, together with the carbon atom to which they are attached, form a 3- to 7-membered ring which may contain one or two oxygen atoms or a group $NR_{35}$ in which $R_{35}$ is hydrogen, $C_1$-$C_4$alkyl, or $C_1$-$C_4$alkylcarbonyl;

$R_{31}$, $R_{32}$, $R_{33}$ and $R_{34}$ independently of one another are hydrogen or $C_1$-$C_4$alkyl, or $R_{31}$ and $R_{32}$ or $R_{33}$ and $R_{34}$, together with the carbon atom to which they are attached, form a 3- to 7-membered ring which may contain one or two oxygen atoms or a group $NR_{36}$ in which $R_{36}$ is hydrogen or $C_1$-$C_4$alkyl;

$Y_2$ is oxygen, —NH—, the group

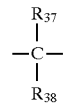

or the group

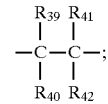

$R_{37}$ and $R_{38}$ independently of one another are hydrogen or $C_1$-$C_4$alkyl; or $R_{37}$ and $R_{38}$, together with the carbon atom to which they are attached form a 3- to 7-membered ring which may contain one or two oxygen atoms or a group $NR_{35}$ in which $R_{35}$ is hydrogen, $C_1$-$C_4$alkyl or $C_1$-$C_4$alkylcarbonyl;

$R_{39}$, $R_{40}$, $R_{41}$ and $R_{42}$ independently of one another are hydrogen or $C_1$-$C_4$alkyl, or $R_{39}$ and $R_{40}$ or $R_{41}$ and $R_{42}$, together with the carbon atom to which they are attached, form a 3- to 7-membered ring which may contain one or two oxygen atoms or a group $NR_{43}$ in which $R_{43}$ is hydrogen or $C_1$–$C_4$alkyl;

Z is the group $$-\underset{R_{45}}{\overset{R_{44}}{\underset{|}{\overset{|}{C}}}}-$$

or the group $$-\underset{R_{47}}{\overset{R_{46}}{\underset{|}{\overset{|}{C}}}}-\underset{R_{49}}{\overset{R_{48}}{\underset{|}{\overset{|}{C}}}}-;$$

$R_{44}$, $R_{45}$, $R_{46}$, $R_{47}$, $R_{48}$ and $R_{49}$ independently of one another are hydrogen or methyl; and p is 0 or 1, to give the corresponding amino compounds, with r in the compound of the formula Ia preferably being 1 or 2 and $R_2$ preferably being hydrogen, halogen, $C_1$–$C_6$alkyl, $C_1$–$C_6$alkoxy, $C_1$–$C_6$haloalkoxy or cyano.

From this group of compounds of the formula Ia, particular emphasis should be placed on those in which $R_2$ is hydrogen, halogen, methyl, difluoromethoxy, trifluoromethoxy or cyano, in which case, in particular, p is 1 and $Y_1$ and $Y_2$ are oxygen. In very particularly preferred compounds of the formula Ia from this group, Z is the group $$-\underset{R_{45}}{\overset{R_{44}}{\underset{|}{\overset{|}{C}}}}-,$$

in which $R_{44}$ and $R_{45}$ are preferably methyl.

A further subgroup of compounds of the formula I corresponds to the formula Ib (Ib)

in which $Y_1$, $Y_2$, Z, p and $R_{28}$ are as defined under formula Ia and $R_{50}$ is hydrogen or halogen; and $R_{51}$, is hydrogen, halogen, methyl, difluoromethoxy, trifluoromethoxy or cyano, and preferably $R_{50}$ is hydrogen, $R_{51}$, is chlorine and $R_{28}$ is allyl.

If the compounds of the formula I contain an asymmetric centre, then this means that the compounds may occur in the form of optical isomers. Some compounds of the formula I may occur in tautomeric forms (e.g. keto-enol tautomerism). If there is an aliphatic C=C double bond, then geometric isomerism (E form or Z form) may also occur. Furthermore, exo-endo configurations are also possible. The formula I therefore comprises all possible stereoisomers in the form of enantiomers, tautomers, diastereomers, E/Z isomers or mixtures thereof.

In the above definitions the term halogen refers to fluorine, chlorine, bromine and iodine, preferably to fluorine, chlorine and bromine.

Alkyl is methyl, ethyl, isopropyl, n-propyl, n-butyl, isobutyl, sec-butyl, tert-butyl and the various isomeric pentyl, hexyl, heptyl, octyl, nonyl, decyl, undecyl and dodecyl radicals.

Examples of haloalkyl are fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferred haloalkyls are trichloromethyl, difluorochloromethyl, trifluoromethyl and dichlorofluoromethyl.

Examples of alkoxy are methoxy, ethoxy, propyloxy, isopropyloxy, n-butyloxy, isobutyl-oxy, s-butyloxy and t-butyloxy; preferred alkoxys are methoxy and ethoxy.

Examples of haloalkoxy are fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferred haloalkoxys are difluoromethoxy, 2-chloroethoxy and trifluoromethoxy.

Examples of alkylthio are methylthio, ethylthio, propylthio, isopropylthio, n-butylthio, isobutylthio, s-butylthio, t-butylthio or the isomeric pentylthios, preferably methylthio and ethylthio.

Alkenyl is straight-chain or branched alkenyl such as, for example, vinyl, allyl, methallyl, 1-methylvinyl, 2-buten-1-yl, pentenyl, 2-hexenyl or 3-heptenyl. Preference is given to alkenyl radicals having a chain length of 2 or 3 carbon atoms.

The alkynyl radicals occurring in the definitions of the substituents may be straight-chain or branched, examples being propargyl, 3-butynyl, 1-methylpropargyl, 1-pentynyl or 2-hexynyl.

Examples of cycloalkyl are cyclopropyl, dimethylcyclopropyl, cyclobutyl, cyclopentyl, methylcyclopentyl, cyclohexyl and cycloheptyl, preferably cyclopropyl, cyclopentyl or cyclohexyl.

Examples of alkoxycarbonyl are methoxycarbonyl, ethoxycarbonyl, n-propyloxycarbonyl, isopropyloxycarbonyl and n-butyloxycarbonyl, preferably methoxycarbonyl and ethoxycarbonyl.

Examples of alkoxyalkyl are methoxymethyl, ethoxymethyl, propyloxymethyl, methoxyethyl, ethoxyethyl, propyloxyethyl, methoxypropyl, ethoxypropyl or propyloxypropyl.

Examples of alkylthioalkyl are methylthiomethyl, ethylthiomethyl, methylthioethyl, ethylthioethyl or isopropylthioethyl.

Examples of alkylaminoalkyl are methylaminoethyl, dimethylaminoethyl, ethylaminoethyl or diethylaminoethyl.

Examples of cyanoalkyl are cyanomethyl, cyanoethyl or cyanopropyl.

Examples of halocycloalkyl are 2,2-dichlorocyclopropyl and pentachlorocyclohexyl.

Examples of alkylsulfonyl are methylsulfonyl, ethylsulfonyl, propylsulfonyl and butylsulfonyl. Methyl- and ethylsulfonyl are preferred.

Phenyl on its own or as part of a substituent such as phenoxy, phenylthio, phenoxycarbonyl, phenylaminocarbonyl, benzyl or benzoyl can in general be unsubstituted or substituted by further substituents. In this case the substituents may be in the ortho, meta and/or para position. Preferred substituent configurations are the positions ortho and para to the point at which the ring is joined. Preferred substituents are halogen atoms.

Examples of aralkyl are benzyl, phenethyl, 3-phenylpropyl, α-methylbenzyl, phenbutyl and α,α-dimethylbenzyl.

Examples of aryl are phenyl, tetralin, indene, naphthalene, azulene and anthracene.

Examples of heteroaryl are pyrrole, furan, thiophene, oxazole, thiazole, pyridine, pyrazine, pyrimidine, pyridazine, indole, purine, quinoline and isoquinoline.

Examples of heterocycloalkyl are oxirane, oxetane, azetidine, azirine, 1,2-oxathiolane, pyrazoline, pyrrolidine, piperidine, piperazine, morpholine, dioxolane, tetrahydropyran, tetrahydrofuran and tetrahydrothiophene.

The reaction according to the invention is preferably carried out in the liquid phase, in particular using a pulverulent catalyst, either continuously or batchwise as a liquid-phase hydrogenation or in a bubble column or using a formed catalyst in a trickle bed.

Furthermore, the reaction can be carried out in the gas phase using a pulverulent catalyst in a fluidized bed or using a formed catalyst in a fixed bed. The examples which follow illustrate the present invention in more detail.

PREPARATION EXAMPLES

Example H1

Preparation of a 5% Pt-1% Pb-CaCO$_3$ catalyst 5 g of a 5% Pt/CaCO$_3$ catalyst are suspended in 20 ml of water and subsequently 2 ml of a lead acetate solution (0.091 g of Pb(OAc)$_2$·3H$_2$O; corresponding to 1% Pb) are added slowly at room temperature. The mixture is stirred at room temperature for 10 minutes and then its temperature is raised to 80° C. for 40 minutes. The solid product is filtered off, washed with water and dried at a temperature of 80° C. in vacuo to give the catalyst having a composition of 4.87% Pt and 1% Pb.

Example H2

Preparation of allyl 3-aminobenzoate

In a stirred autoclave, 1 g of a catalyst prepared according to Example H1 is added to a solution of 10.4 g of allyl 3-nitrobenzoate in 100 ml of tetrahydrofuran, and the mixture is hydrogenated for 8 hours at a temperature of 120° C. and at a hydrogen pressure of 20 bar. After filtering off the catalyst and distilling off the solvent, 9.1 g of crude product are obtained having a content of 88.8% of allyl 3-aminobenzoate in a yield of 91% of theory.

$^1$H—NMR (CDCl$_3$, 250 MHz): 3.68 ppm (s, 2H); 4.75 ppm (d, 2H); 5.25 ppm (q, 2H); 5.95 ppm (m, 1H); 7.15 ppm (m, 1H); 7.25 ppm (m, 1H); 7.35 ppm (m, 1H).

Example H3

Preparation of allyl 2-(2-chloro-5-aminobenzoyloxy)-2-methylprolpionate

In a stirred autoclave, 0.1 g of a catalyst prepared according to Example H1 is added to a solution of 10 g of allyl 2-(2-chloro-5-nitrobenzoyloxy)-2-methylpropionate in 80 ml of tetrahydrofuran and 20 ml of n-propanol, and the mixture is hydrogenated for 15 hours at a temperature of 140° C. and at a hydrogen pressure of 20 bar. After cooling the mixture to room temperature and flushing the stirred autoclave with nitrogen, the catalyst is filtered off. 126.8 g (incl. rinsing solvent) are obtained of a solution having a content of 6.58% of allyl 2-(2-chloro-5-aminobenzoyloxy)-2-methylpropionate (yield: 92.7% of theory).

$^1$H—NMR (CDCl$_3$, 250 MHz): 1.62 ppm (s, 6H); 3.65 ppm (s, 2H); 4.6 ppm (d, 2H); 5.2 ppm (q, 2H); 5.85 ppm (m, 1H); 6.65 ppm (m, 1H); 7.0 ppm (m, 1H); 7.1 ppm (m, 1H).

Example H4

Preparation of allyl 2-(2-chloro-5-aminobenzoyloxy)-2-methylpropionate

In a stirred autoclave, 0.1 g of a catalyst prepared according to Example H1 is added to a solution of 10 g of allyl 2-(2-chloro-5-nitrobenzoyloxy)-2-methylpropionate in 80 ml of tetrahydrofuran and 20 ml of n-propanol, 6 mg (0.1 mol %) of FeCl$_2$4H$_2$O are added in addition and the mixture is hydrogenated for 7 hours at a temperature of 140° C. and at a hydrogen pressure of 20 bar. After cooling to room temperature and flushing the stirred autoclave with nitrogen, the catalyst is filtered off. 117.3 g are obtained of a solution having a content of 7.26% of allyl 2-(2-chloro-5-aminobenzoyloxy)-2-methylpropionate (yield: 94.6% of theory).

$^1$H—NMR (CDCl$_3$, 250 MHz): 1.62 ppm (s, 6H); 3.65 ppm (s, 2H); 4.6 ppm (d, 2H); 5.2 ppm (q, 2H); 5.85 ppm (m, 1H); 6.65 ppm (m, 1H); 7.0 ppm (m, 1H); 7.1 ppm (m, 1H).

Example H5

Preparation of allyl 2-(2-chloro-5-aminobenzoyloxy)-2-methylpropionate

In a stirred autoclave, 0.33 g of a catalyst prepared according to Example H1 is added to a solution of 65.5 g of allyl 2-(2-chloro-5-nitrobenzoyloxy)-2-methylpropionate in 370 g of methyl ethyl ketone, 0.2 g (0.5 mol %) of FeCl$_2$4H$_2$O and 22 mg (0.1 mol %) of tetramethylammonium chloride are added in addition, and the mixture is hydrogenated for 5 hours at a temperature of 140° C. and at a hydrogen pressure of 15 bar. After cooling and flushing the stirred autoclave with nitrogen, the catalyst is filtered off and rinsed with 40 g of methyl ethyl ketone. 435.5 g are obtained of a solution having a content of 13.22% of allyl 2-(2-chloro-5-aminobenzoyloxy)-2-methylpropionate (yield: 96.8 % of theory).

$^1$H—NMR (CDCl$_3$, 250 MHz) 1.62 ppm (s,2H); 4.6 ppm (d,2H); 5.2 ppm (q,2H); 5.85 ppm (m,1H); 6.65 ppm (m,1H); 7.0 ppm (m,1H); 7.1 ppm (m,1H)

Example H6

Preparation of propargyl 3-aminobenzoate

In a stirred autoclave, 0.5 g of a catalyst prepared according to Example H1 and containing 0.182 g of Pb(OAc)$_2$ 3H$_2$O (corresponding to 2% Pb), and 50 mg (0.5mol %) of FeCl$_2$4H$_2$O are added to a solution of 10.4 g of propargyl 3-nitrobenzoate in 100 ml of methyl ethyl ketone. The mixture is then hydrogenated for 14 hours at a temperature of 140° C. and at a hydrogen pressure of 20 bar. The catalyst is filtered off, the solvent is distilled off and the remaining mixture is purified by column chromatography to give 5.8 g of propargyl 3-aminobenzoate. The content of allyl 3-aminobenzoate according to $^1$H—NMR is 18%.

$^1$H—NMR (CDCl$_3$,250 MHz) of propargyl 3-aminobenzoate: 2.54 ppm (s,1H); 3.84 ppm (s,2H); 4.93 ppm (s,2H); 6.93 ppm (m,1H); 7.23 ppm (m,1H); 7.5 ppm (m,2H)

Examples H7 –H20 below are carried out analogously to Example H4. Examples 7 and 10 use tetrahydrofuran and Examples 8 and 9 use methyl ethyl ketone as solvent instead of THF/n-propanol. Example 19 is carried out analogously to Example H6. The $^1$H—NMR spectra (250 MHz) are recorded, with the exception of Example H7 (d-DMSO) in CDCl$_3$.

Example H7

Preparation of 4-aminophenyl vinyl ether

Yield: 94%; $^1$H—NMR data: 4.1 ppm (d,1H); 4.33 ppm (d,1H); 4.72ppm (s,2H); 6.38 ppm (m,2H); 6.50 ppm (m,1H); 6.57ppm (m,2H).

Example H8

Preparation of ethyl 4-aminocinnamate

Yield: 99%; $^1$H—NMR data: 1.30 (t,3H); 3.94 (s,2H); 4.23 (q,2H); 6.23 (d,1H); 6.64 (d,2H); 7.34 (d,2H); 7.58 (d,1H).

Example H9

Preparation of allyl 2-(2-chloro-5-aminophenoxy)-2-methylpropionate

Yield: 98%; $n_D$ (22° C.)=1.5442; $^1$H—NMR data: 1.61 (s,6H); 3.65 (broad,2H); 4.69 (d,2H); 5.29 (m,2H); 5.91 (m,1H); 6.32 (m,2H); 7.08 (d,1H).

Example H10

Preparation of 4-aminophenyl allyl ether

Yield: 99%; $^1$H—NMR data: 3.40 (s,2H); 4.48 (m,2H); 5.28 (m,2H); 6.04 (m,1H); 6.64 (m,2H); 6.78 (m,2H).

Example H11

Preparation of N-allyl-2-(2-chloro-5-aminobenzoyloxy)-2-methylpropionamide

Yield: 70%; $^1$H—NMR data: 1.81 (s,6H); 3.92 (m,2H); 4.14 (m,2H); 5.17 (m,2H); 5.84 (m,1H); 6.77 (m,2H); 7.05 (m,1H); 7.15 (m,1H).

Example H12

Preparation of 2-butenyl 2-(2-chloro-5-aminobenzoyloxy)-2-methylpropionate

Yield: 98%; $n_D(20)$=1.5261; $^1$H—NMR data: 1.68 (m,9H); 3.75 (broad,2H); 4.68 (m,2H); 5.58 (m,1H); 5.79 (m,1H); 6.67 (d,1H); 7.10 (d,1H); 7.20 (d,1H).

Example H13

Preparation of 2-cyano-4-fluoro-5-aminophenyl allyl ether

Yield: 64%; m.p. 70°–71°) C.; $^1$H—NMR data: 4.35 (s,2H); 4.55 (s, 2H); 5.34 (q,2H); 6.01 (m,1H); 6.29 (d, 1H); 7.12 (d,1H).

Example H14

Preparation of allyl 2-(2-chloro-4-fluoro-5-aminophenoxy)-2-methyl-propionate

Yield: 94%; $n_D$(22° C.): 1.5227; $^1$H—NMR data: 1.60 (s,6H); 3.70 (s, 2H); 4.68 (d,2H); 5.34 (q,2H); 5.94 (m,1H); 6.5 (d,1H); 6.98 (d,1H).

Example H15

Preparation of allyl 2-(2-bromo-5-aminophenoxy)-2-methylpropionate

Yield: 98%; $^1$H—NMR data: 1.71 (s, 6H); 4.17 (broad, 2H); 4.70 (d, 2H); 5.31 (m,2H); 5.94 (m,1H); 6.64 (m,1H); 7.08 (m,1H); 7.30 (m,1H).

Example H16

Preparation of 2-chloro-4- fluoro-5-aminophenyl allyl ether

Yield: 88%; $n_D$(22° C.): 1.5587; $^1$H—NMR data: 3.72 (s,2H); 4.00 (d,2H); 5.36 (q,2H); 6.02 (m,1H); 6.35 (d,1H); 7.02 (d,1H).

Example H17

Preparation of allyl 2-chloro-4-fluoro-5-aminobenzoate

Yield: 83%; $n_D$(22° C.): 1.5621; $^1$H—NMR data: 3.86 (s,2H); 4.77 (d,2H); 5.35 (q,2H); 6.01 (m,1H); 7.08 (d,1H); 7.35 (d,1H).

Example H18

Preparation of 5-amino-6-fluoro-3-allyl-3H-benzothiazol-2-one

Yield: 94%; m.p. : 66°–68° C.; $^1$H—NMR data: 3.86 (s,2H); 3.98 (s,2H); 5.21 (m,2H); 5.85 (m,1H); 6.47 (d,1H); 7.08 (d,1H).

Example H19

Preparation of 5-amino-6-fluoro-3-propargyl-3H-benzothiazol-2-one

Yield: 80%; m.p. :142°–144° C.; $^1$H—NMR data: 2.26 (s,1H); 3.92 (s,2H); 4.61 (s, 2H); 6.66 (d1H); 7.05 (d, 1H).

Example H20

Preparation of allyl 2-(2-chloro-4-fluoro-5-aminobenzoyloxy)-2-methyl-propionate Yield: 70%; $n_D$ (22° C.)=1.5132; $^1$H—NMR data: 1.71 (s,6H); 3.81 (broad,2H); 4.65 (d,2H); 5.26 (q,2H); 5.91 (m,1H); 7.09 (d,1H); 7.29 (d1H).

Example 21

Preparation of a 5% Pt-1%Pb—$SiO_2$ catalyst 5 g of a commercial Pt—$SiO_2$ catalyst are suspended in 40 ml of deionized $H_2O$, and 2 ml of a lead acetate solution (0.091 g of Pb(Ac)$_{2\times 3}$$H_2O$: corresponding to 1% Pb) are added slowly at room temperature. The mixture is stirred at room temperature for 10 min and Using the known processes, nitrated aromatic compounds which are substituted by groups comprising unsaturated carbon-carbon bonds can be reduced to the corresponding amino compounds only with a high degree of complexity and/or in an economically unsatisfactory manner. It is therefore the aim of the present invention to provide a technically, economically and ecologically improved process, capable of general utilization, for the preparation of aromatic amino compounds which are substituted by groups comprising unsaturated carbon-carbon bonds.

TABLE 1

Table 1: Compounds of the formula Ic:

| Comp. No. | $R_{51}$ | $R_{50}$ | $Y_3$ | phys. data |
|---|---|---|---|---|
| 1.1 | Cl | Cl | —OC(CH$_3$)$_2$COO—CH$_2$—CH═CH$_2$ | |
| 1.2 | Cl | F | —OC(CH$_3$)$_2$COO—CH$_2$—CH═CH$_2$ | |
| 1.3 | Cl | H | (rac-)OC(CH$_3$)$_2$COOCH(CH$_3$)—CH═CH$_2$ | |
| 1.4 | Cl | H | —OC(CH$_3$)$_2$COOCH$_2$—CH═CH$_2$ | $n_D^{33}$ 1.5435 |
| 1.5 | CN | H | —OC(CH$_3$)$_2$COOCH$_2$—CH═CH$_2$ | |
| 1.6 | Br | H | —OC(CH$_3$)$_2$COO—CH$_2$—CH═CH$_2$ | |
| 1.7 | Br | F | —OC(CH$_3$)$_2$COO—CH$_2$—CH═CH$_2$ | |
| 1.8 | OCF$_3$ | F | (rac-)OCH(CH$_3$)COO—CH$_2$—CH═CH$_2$ | |
| 1.9 | OCF$_3$ | F | (S)—OCH(CH$_3$)—COO—CH$_2$—CH═CH$_2$ | |
| 1.10 | OCF$_3$ | H | (rac-)OCH(CH$_3$)—COO—CH$_2$—CH═CH$_2$ | |
| 1.11 | OCF$_3$ | H | (S)—OC(CH$_3$)$_2$—COO—CH(CH$_3$)—CH═CH$_2$ | |
| 1.12 | OCF$_3$ | H | rac-O—C(CH$_3$)$_2$—COO—CH(CH$_3$)CH═CH$_2$ | |
| 1.13 | Cl | H | (S)—O—C(CH$_3$)$_2$—COO—CH(CH$_3$)CH═CH$_2$ | |
| 1.14 | Cl | F | (S)—O—C(CH$_3$)$_2$—COO—CH(CH$_3$)CH═CH$_2$ | |
| 1.15 | CN | F | (rac-)O—C(CH$_3$)$_2$—COOCH(CH$_3$)CH═CH$_2$ | |
| 1.16 | Cl | H | 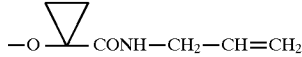 | |
| 1.17 | Cl | H | (rac-)OCH(C$_2$H$_5$)COOCH$_2$CH═CH$_2$ | |
| 1.18 | Cl | H | —OC(C$_2$H$_5$)$_2$COOCH$_2$CH═CH$_2$ | |
| 1.19 | Cl | H | (R)OC(CH$_3$)$_2$COOCH(CH$_3$)CH═CH$_2$ | |
| 1.20 | Br | H | —O—C(CH$_3$)$_2$CONH—CH$_2$—CH═CH$_2$ | |
| 1.21 | Cl | H | —O—CH(CH$_3$)CONH—CH$_2$—CH═CH$_2$ | |
| 1.22 | Cl | H | (S)—O—CH(CH$_3$)CONH—CH$_2$—CH═CH$_2$ | |
| 1.23 | Cl | H | (R)O—CH(CH$_3$)CONH—CH$_2$—CH═CH$_2$ | |
| 1.24 | Cl | F | (S)—O—CH(CH$_3$)CONH—CH$_2$—CH═CH$_2$ | |
| 1.25 | Cl | H |  | |
| 1.26 | Cl | H | (S)—O—[cyclopropyl]—CONH—CH(CH$_3$)—CH═CH$_2$ | |
| 1.27 | Cl | F | —NHCH$_2$CH═CH$_2$ | |
| 1.28 | Cl | H | —O—C(CH$_3$)$_2$CONHCH$_2$CH═CH$_2$ | |
| 1.29 | Cl | H | —O—CH$_2$CONHCH$_2$CH═CH$_2$ | |
| 1.30 | CN | H | —O—CH(CH$_3$)CH═CH$_2$ | |
| 1.31 | Cl | H | (S)—O—CH(CH$_3$)CH═CH$_2$ | |
| 1.32 | Cl | H | (S)O—C(CH$_3$)$_2$—COO—CH(C$_2$H$_5$)—CH═CH$_2$ | |
| 1.33 | Cl | H | (S)—O—C(CH$_3$)$_2$—COOCH(C$_2$H$_5$)—CH═CH$_2$ | |
| 1.34 | Br | Br | —O—C(C$_2$H$_5$)$_2$—COO—CH$_2$—CH═CH$_2$ | |
| 1.35 | Cl | F | —O—CH(C$_4$H$_9$-n)-COO—CH$_2$—CH═CH$_2$ | |
| 1.36 | Cl | Cl | —OC(C$_4$H$_9$-n)$_2$-COOCH$_2$—CH═CH$_2$ | |
| 1.37 | OCF$_3$ | F | —OC(C$_3$H$_7$-n)$_2$-COOCH$_2$—CH═CH$_2$ | |
| 1.38 | CN | F | —OCH(C$_3$H$_7$-i)-COOCH$_2$—CH═CH$_2$ | |
| 1.39 | Cl | F | —O—C(CH$_3$)$_2$—CONH—CH(C$_4$H$_9$-n)-CH═CH$_2$ | |
| 1.40 | Cl | H | (S)O—C(CH$_3$)$_2$—CONH—CH(C$_3$H$_7$-i)-CH═CH$_2$ | |
| 1.41 | Cl | H | —O—CH(CH$_3$)—CH(CH$_3$)COOCH$_2$—CH═CH$_2$ | |
| 1.42 | Cl | H | —O—CH(CH$_3$)—CH$_2$—COO—CH$_2$—CH═CH$_2$ | |
| 1.43 | Cl | H | (S)—O—CH(CH$_3$)—CH$_2$COO—CH$_2$CH═CH$_2$ | |
| 1.44 | Cl | H | (S)—O—CH(CH$_3$)—CH$_2$CONH—CH$_2$CH═CH$_2$ | |
| 1.45 | Cl | F | —O—CH(C$_2$H$_5$)—CH$_2$COOCH$_2$—CH═CH$_2$ | |
| 1.46 | Cl | H | —OCH(C$_4$H$_9$-s)-CH$_2$—COOCH$_2$CH═CH$_2$ | |
| 1.47 | Br | H | —O—CH$_2$—CH(C$_4$H$_9$-n)-COOCH$_2$—CH═CH$_2$ | |
| 1.48 | Cl | F | —O—CH$_2$—C(CH$_3$)$_2$—COO—CH$_2$CH═CH$_2$ | |
| 1.49 | Cl | H | (S)—O—CH$_2$—C(CH$_3$)$_2$—COO—CH(CH$_3$)CH═CH$_2$ | |
| 1.50 | Cl | H |  | |

TABLE 1-continued

Table 1: Compounds of the formula Ic:

$$H_2N-C_6H_2(R_{50})(R_{51})-C(=O)-Y_3 \quad (Ic)$$

| Comp. No. | $R_{51}$ | $R_{50}$ | $Y_3$ | phys. data |
|---|---|---|---|---|
| 1.51 | Cl | H | —O—(cyclopentyl)—COOCH$_2$CH=CH$_2$ | |
| 1.52 | Cl | F | —O—(cyclohexyl)—COOCH(CH$_3$)CH=CH$_2$ | |
| 1.53 | Cl | Cl | —O—(cycloheptyl)—CONCH(C$_2$H$_5$)CH=CH$_2$ | |
| 1.54 | Cl | Cl | —OCH$_2$CH=CH$_2$ | |
| 1.55 | Cl | F | —OCH$_2$CH=CH$_2$ | |
| 1.56 | CN | F | —OCH$_2$CH=CH$_2$ | |
| 1.57 | Br | Br | —OCH(CH$_3$)CH=CH$_2$ | |
| 1.58 | I | H | —OC(CH$_3$)$_2$CH=CH$_2$ | |
| 1.59 | OCF$_3$ | H | —OC(CH$_3$)$_2$CH=CH$_2$ | |
| 1.60 | OCHF$_2$ | F | —OC(CH$_3$)$_2$CH=CH$_2$ | |
| 1.61 | Cl | H | —OC(CH$_3$)$_2$CH=CH$_2$ | |
| 1.62 | Cl | H | —OCH(CH$_3$)CH=CH$_2$ | |
| 1.63 | Cl | H | —OCH$_2$—CH=CH$_2$ | |
| 1.64 | CN | H | —OC(CH$_3$)$_2$CH=CH$_2$ | |
| 1.65 | Cl | H | (S—)—OCH(CH$_3$)CH=CH$_2$ | |
| 1.66 | Cl | F | —O—(cyclopropyl)—CH=CH$_2$ | |
| 1.67 | Cl | H | —O—(cyclopentyl)—CH=CH$_2$ | |
| 1.68 | Cl | H | —O—(cycloheptyl)—CH=CH$_2$ | |
| 1.69 | Cl | H | —NH—CH$_2$—CH=CH$_2$ | |
| 1.70 | Cl | H | —NH—CH(CH$_3$)CH=CH$_2$ | |
| 1.71 | Cl | H | —NH—CH(C$_4$H$_9$-n)CH=CH$_2$ | |
| 1.72 | Cl | F | —NH—CH$_2$CH=CH$_2$ | |
| 1.73 | Cl | F | —O—CH$_2$—(cyclohexyl)—COOCH$_2$CH=CH$_2$ | |
| 1.74 | Cl | H | —OCH(CH$_3$)—(cyclohexyl)—COOCH$_2$CH=CH$_2$ | |
| 1.75 | Cl | H | —OC(CH$_3$)$_2$—(cyclopropyl)—COOCH$_2$CH=CH$_2$ | |
| 1.76 | CN | F | —OCH(CH$_3$)—(cyclopentyl)—COOCH(CH$_3$)CH=CH$_2$ | |

TABLE 1-continued

Table 1: Compounds of the formula Ic:

| Comp. No. | $R_{51}$ | $R_{50}$ | $Y_3$ | phys. data |
|---|---|---|---|---|
| 1.77 | Cl | Cl | —OCH$_2$—⬠—COOCH$_2$CH=CH$_2$ | |
| 1.78 | Cl | Br | —OCH$_2$—⬠—CONHCH$_2$CH=CH$_2$ | |
| 1.79 | OCF$_3$ | F | —OCH(CH$_3$)—◇—CONHCH$_2$CH=CH$_2$ | |
| 1.80 | OCHF$_2$ | H | —OCH$_2$—⬠—COOCH$_2$CH=CH$_2$ | |
| 1.81 | Cl | Cl | —OCH$_2$—⬡—COOCH$_2$CH=CH$_2$ | |
| 1.82 | OCHF$_2$ | H | (S)—O—▽—COOCH(CH$_3$)CH=CH$_2$ | |
| 1.83 | OCF$_3$ | H | (S)—O—▽—COOCH(CH$_3$)CH=CH$_2$ | |
| 1.84 | CN | H | (rac)—O—▽—COOCH(CH$_3$)CH=CH$_2$ | |
| 1.85 | I | I | —O—▽—COOCH$_2$CH=CH$_2$ | |
| 1.86 | I | F | —OC(CH$_3$)$_2$CONHCH$_2$CH=CH$_2$ | |
| 1.87 | Cl | H | —OC(CH$_3$)$_2$COOCH$_2$CH=CH$_2$ | |
| 1.88 | Cl | F | (S)—O—▽—CONHCH(CH$_3$)CH=CH$_2$ | |

What is claimed is:

1. A process for the preparation of aromatic amino compounds which are substituted by at least one group comprising at least one unsaturated carbon-carbon bond, by catalytic hydrogenation of corresponding aromatic nitro compounds in the presence of a modified noble metal catalyst, which comprises using as noble metal catalyst platinum which is modified with a metal selected from the group consisting of lead, mercury, bismuth, germanium, cadmium, arsenic, antimony, silver and gold.

2. A process according to claim 1, wherein lead is used as modifying metal.

3. A process according to claim 1, wherein the noble metal catalyst is used in a quantity of from 0.1 to 5% by weight, based on the aromatic nitro compound employed.

4. A process according to claim 1, wherein a noble metal catalyst is used in which the weight ratio of platinum to modifying metal is from 1:0.001 to 1:1.

5. A process according to claim 4, wherein the weight ratio of platinum to the modifying metal is from 1:0.1 to 1:0.5.

6. A process according to claim 1, wherein a noble metal catalyst is used which contains from 1 to 10% by weight of platinum.

7. A process according to claim 1, wherein a noble metal catalyst is used in which the platinum has been applied in metallic or oxidized form to a support.

8. A process according to claim 7, wherein the support used is active charcoal, silicic acid, silica gel, alumina, calcium carbonate, calcium phosphate, calcium sulfate, barium sulfate, titanium oxide, magnesium oxide, iron oxide, lead oxide, lead sulfate or lead carbonate.

9. A process according to claim 8, wherein the support used is active charcoal, alumina or calcium carbonate.

10. A process according to claim 1, wherein a noble metal catalyst is used which comprises, as promoter, a compound of iron, ruthenium, cobalt, copper or manganese.

11. A process according to claim 10, wherein the promoter is used in a quantity of from 0.001 to 10% by weight, based on the aromatic nitro compound employed.

12. A process according to claim 10, wherein an iron salt is used as promoter.

13. A process according to claim 12, wherein the iron salt used is $FeCl_2 \cdot 4H_2O$.

14. A process according to claim 1, wherein a noble metal catalyst is used which comprises as co-promoters ion pairs or salts which are soluble in organic solvents.

15. A process as claimed in claim 14, wherein for the salts and ion pairs the cation used is $(C_1-C_6 alkyl)_4 N^+$ or

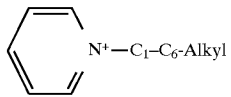

and as anion $Cl^{31}$, $Br^{31}$, $F^{31}$, $BF_4^-$, $PF_6^-$, $NO_3^-$, $F_3CSO_3^-$, $BPh_4^-$, $PhCOO^-$,

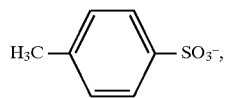

$CH_3SO_3^-$ and $F_3COO^-$.

16. A process according to claim 14, wherein quaternary ammonium bases are used as co-promoters.

17. A process according to claim 16, wherein tetramethylammonium chloride is used as quaternary ammonium base.

18. A process according to claim 14, wherein the co-promoters are used in a quantity of from 0.001 to 10% by weight, based on the aromatic nitro compound employed.

19. A process according to claim 1, which is carried out at a pressure of from 1 to 100 bar and at a temperature of from +20° to +160° C.

20. A process according to claim 1, wherein the aromatic nitro compound corresponds to the formula I

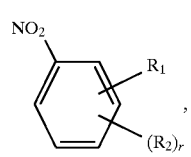

in which

R$_1$ is a group comprising at least one unsaturated carbon-carbon bond;

r is 1, 2, 3, or 4;

R$_2$ is hydrogen, $C_1-C_{12}$alkyl, $C_1-C_{12}$haloalkyl, $C_1-C_2$hydroxyalkyl, $C_1-C_6$cyanoalkyl, $C_3-C_8$cycloalkyl, $C_6-C_{16}$aryl, $C_7-C_{16}$aralkyl, $C_3-C_6$heterocycloalkyl, $C_3-C_6$heteroaryl, $C_4-C_{16}$heteroaralkyl, halogen, cyano, COR$_3$, X$_1$R$_4$, —COR$_8$,

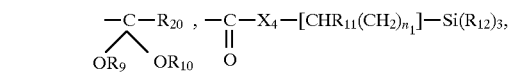

—N(R$_{13}$)—SO$_2$—R$_{14}$,

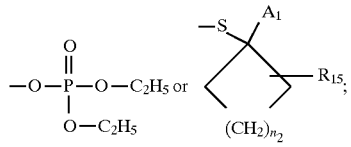

A$_1$ is cyano or —COR$_{16}$;

R$_3$ is halogen, X$_2$—R$_5$, amino, $C_1-C_4$alkylamino, di-$C_1-C_4$alkylamino, $C_2-C_4$haloalkyl-amino, di-$C_2-C_4$-haloalkylamino, $C_1-C_4$alkoxyalkylamino, di-$C_1-C_4$-alkoxyalkylamino, $C_2-C_4$alkenylamino, diallylamino, —N-pyrrolidino, —N-piperidino, —N-morpholino, —N-thiomorpholino, —N-piperidazino;

R$_4$ is hydrogen, $C_1-C_{10}$alkyl, $C_1-C_4$alkoxy-$C_1-C_4$alkyl, $C_1-C_4$alkylthio-$C_1-C_4$alkyl, di-$C_1-C_4$alkylamino-$C_1-C_4$alkyl, halo-$C_1-C_8$alkyl, $C_2-C_8$alkenyl, halo-$C_2-C_8$alkenyl, $C_3-C_8$alkynyl, $C_3-C_7$cycloalkyl, halo-$C_3-C_7$cycloalkyl, $C_1-C_8$alkylcarbonyl, allylcarbonyl, $C_3-C_7$cycloalkylcarbonyl, benzoyl which is unsubstituted or is substituted on the phenyl ring by up to three identical or different substituents consisting of halogen, $C_1-C_4$alkyl, halo-$C_1-C_4$alkyl, halo-$C_1-C_4$alkoxy or $C_1-C_4$alkoxy; or is furanoyl, thienyl; or is $C_1-C_4$alkyl substituted by phenyl, halophenyl, $C_1-C_4$alkylphenyl, $C_1-C_4$alkoxyphenyl, halo-$C_1-C_4$alkylphenyl, halo-$C_1-C_4$alkoxyphenyl, $C_1-C_6$alkoxycarbonyl, $C_1-C_4$alkoxy-$C_1-C_8$alkoxycarbonyl, $C_2-C_8$alkenyloxycarbonyl, $C_3-C_8$alkynyloxycarbonyl, $C_1-C_8$alkylthiocarbonyl, $C_2-C_8$alkenylthiocarbonyl, $C_3-C_8$alkynylthiocarbonyl, carbamoyl, mono-$C_1-C_4$alkylaminocarbonyl, di-$C_1-C_4$-alkylaminocarbonyl; or is phenyl-aminocarbonyl which is unsubstituted or is substituted on the phenyl up to three times by identical or different substituents consisting of halogen, $C_1-C_4$alkyl, halo-$C_1-C_4$alkyl, halo-$C_1-C_4$alkoxy or $C_1-C_4$alkoxy or is substituted once by cyano, or is dioxolan-2-yl which is unsubstituted or is substituted by one or two $C_1-C_4$alkyl groups; or is dioxan-2-yl, which is unsubstituted or is substituted by one or two $C_1-C_4$alkyl groups, or is $C_1-C_4$alkyl which is substituted by cyano, carboxyl or $C_1-C_8$alkylthio-$C_1-C_8$alkoxy-carbonyl;

R$_5$ is hydrogen, $C_1-C_{10}$alkyl, $C_1-C_4$alkoxy-$C_1-C_4$alkyl, halo-$C_1-C_8$alkyl, $C_1-C_{10}$alkylthio-$C_1-C_4$alkyl, di-$C_1-C_4$alkylamino-$C_1-C_4$alkyl, cyano-$C_1-C_8$alkyl, $C_2-C_8$alkenyl, halo-$C_2-C_8$alkenyl, $C_3-C_8$alkynyl, $C_3-C_7$cycloalkyl, $C_3-C_7$cycloalkyl-$C_1-C_4$alkyl, halo-$C_3-C_7$cycloalkyl or benzyl which is unsubstituted or is substituted on the phenyl ring by up to three identical or different substituents consisting of halogen, $C_1-C_4$alkyl, halo-$C_1-C_4$alkyl, halo-$C_1C_4$alkoxy or $C_1-C_4$alkoxy, or is an alkali metal, alkaline earth metal or ammonium ion, or is the group —[CHR$_6$(CH$_2$)$_{n_3}$]—COOR$_7$;

R$_6$ is hydrogen or $C_1-C_4$alkyl;

R$_7$ is hydrogen, $C_1-C_6$alkyl, $C_2-C_8$alkenyl, $C_3-C_8$alkynyl, $C_1-C_8$alkoxy-$C_2-C_8$alkyl, $C_1-C_8$alkylthio-$C_1-C_8$alkyl or $C_3-C_7$cycloalkyl;

$R_8$ and $R_{20}$ independently of one another are hydrogen, $C_1$–$C_4$alkyl, halo-$C_1$–$C_4$alkyl or $C_1$–$C_4$alkoxy-$C_1$–$C_4$alkyl;

$R_9$ and $R_{10}$ independently of one another are each $C_1$–$C_4$alkyl, $C_2$–$C_4$haloalkyl or $C_2$–$C_8$-alkoxyalkyl, or $R_9$ and $R_{10}$ together are an ethano, propano or a cyclohexane-1,2-diyl bridge, these groups either being unsubstituted or being able to be substituted by one or two $C_1$–$C_4$alkyl, $C_1$–$C_4$haloalkyl or $C_1$–$C_4$hydroxyalkyl groups;

$R_{11}$ is hydrogen, $C_1$–$C_5$alkyl or $C_3$–$C_7$alkenyl;

$R_{12}$ is $C_1$–$C_8$alkyl;

$R_{13}$ is hydrogen, $C_1$–$C_5$alkyl, benzyl, halo-$C_1$–$C_4$alkyl, $C_2$–$C_8$alkenyl or $C_3$–C8alkynyl;

$R_{14}$ is $C_1$–$C_6$alkyl, halo-$C_1$–$C_5$alkyl or di-$C_1$–$C_4$alkylamino;

$R_{15}$ is hydrogen, fluorine, chlorine, bromine, $C_1$–$C_4$alkyl or trifluoromethyl;

$R_{16}$ is $X_3$—$R_{17}$, amino, $C_1$–$C_4$alkylamino, di-$C_1$–$C_4$alkylamino, $C_2$–$C_4$haloalkylamino, di-$C_2$–$C_4$haloalkylamino, $C_1$–$C_4$alkoxyalkylamino, di-$C_1$–$C_4$alkoxyalkylamino, $C_2$–$C_4$alkenylamino, diallylamino, —N-pyrrolidino, —N-piperidino, —N-morpholino, —N-thiomorpholino, —N-piperidazino, the group —O—N=C—(CH$_3$)—CH$_3$, —O—CH$_2$—CH$_2$—O—N=C(CH$_3$)—CH$_3$ or the group —N(OR$_{24}$)—R$_{22}$;

$R_{17}$ is hydrogen, $C_1$–$C_{10}$alkyl, $C_1$–$C_4$alkoxy-$C_1$–$C_4$alkyl, halo-$C_1$–$C_8$alkyl, $C_1$–$C_{10}$-alkylthio-$C_1$–$C_4$alkyl, di-$C_1$–$C_4$alkylamino-$C_1$–$C_4$alkyl, cyano-$C_1$–$C_8$alkyl, $C_2$$C_8$alkenyl, halo-$C_2$–$C_8$alkenyl, $C_3$–$C_8$alkynyl, $C_3$–$C_7$cycloalkyl, $C_3$–$C_7$cycloalkyl-$C_1$–$C_4$alkyl, halo-$C_3$–$C_7$cycloalkyl or benzyl which is unsubstituted or is substituted on the phenyl ring by up to three identical or different substituents consisting of halogen, $C_1$–$C_4$alkyl, halo-$C_1$–$C_4$alkyl, halo-$C_1$–$C_4$alkoxy or $C_1$–$C_4$alkoxy, or is an alkali metal, alkaline earth metal or ammonium ion, or is the group —[CHR$_{25}$—(CH$_2$)$_m$]—COOR$_{26}$ or the group [CHR$_{27}$—(CH$_2$)$_t$—Si(R$_{23}$)$_3$];

$R_{22}$ is hydrogen or $C_1$–$C_4$alkyl;

$R_{23}$ is $C_1$–$C_4$alkyl, halo-$C_1$–$C_4$alkyl or $C_1$–$C_4$alkoxy-$C_1$–$C_4$alkyl;

$R_{24}$ and $R_{25}$ independently of one another are hydrogen or $C_1$–$C_4$alkyl;

$R_{26}$ independently at each occurrence is hydrogen, $C_1$–$C_6$alkyl, $C_2$–$C_8$alkenyl, $C_3$–$C_8$alkynyl, $C_1$–$C_8$alkoxy-$C_2$–$C_8$alkyl, $C_1$–$C_8$alkylthio-$C_1$–$C_8$alkyl or $C_3$–$C_7$cycloalkyl;

$R_{27}$ is hydrogen or $C_1$–$C_4$alkyl;

m is 0, 1, 2, 3 or 4;

t is 0, 1, 2, 3 or 4

$n_1$, $n_2$ and $n_3$ independently of one another are 0, 1, 2, 3 or 4; and $X_1$, $X_2$, $X_3$ and $X_4$ independently of one another are oxygen or sulfur.

21. A process according to claim 20, wherein in the compound of the formula I r is 1 or 2.

22. A process according to claim 20, wherein the unsaturated carbon-carbon bond of the substituent $R_1$ is part of an ester group.

23. A process according to claim 20, wherein in the compound of the formula I $R_2$ is hydrogen, halogen, $C_1$–$C_6$alkyl, $C_1$–$C_6$alkoxy, $C_1$–$C_6$haloalkoxy or cyano.

24. A process according to claim 23, wherein $R_2$ is hydrogen, halogen, methyl, difluoromethoxy, trifluoromethoxy or cyano.

25. A process according to claim 1, wherein the aromatic nitro compound corresponds to the formula Ia

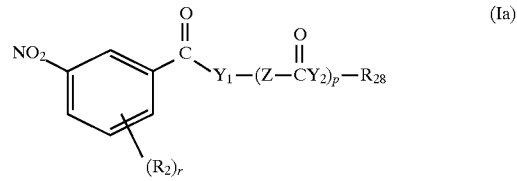

in which $R_2$ and r are as defined under formula I, and $R_{28}$ is $C_2$–$C_6$alkenyl, $C_3$–$C_6$alkynyl, $C_3$–$C_8$cycloalkenyl or $C_6$–$C_8$bicycloalkenyl;

$Y_1$ is oxygen, —NH—, the group

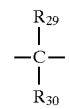

or the group

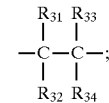

$R_{29}$ and $R_{30}$ independently of one another are hydrogen or $C_1$–$C_4$alkyl; or $R_{29}$ and $R_{30}$, together with the carbon atom to which they are attached, form a 3- to 7-membered ring which may contain one or two oxygen atoms or a group NR$_{35}$ in which R$_{35}$ is hydrogen, $C_1$–$C_4$alkyl, or $C_1$C$_4$alkylcarbonyl;

$R_{31}$, $R_{32}$, $R_{33}$ and $R_{34}$ independently of one another are hydrogen or $C_1$–$C_4$alkyl, or $R_{31}$ and $R_{32}$ or $R_{33}$ and $R_{34}$, together with the carbon atom to which they are attached, form a 3- to 7-membered ring which may contain one or two oxygen atoms or a group NR$_{36}$ in which R$_{36}$ is hydrogen or $C_1$–$C_4$alkyl;

$Y_2$ is oxygen, —NH—, the group

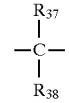

or the group

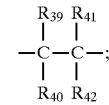

$R_{37}$ and $R_{38}$ independently of one another are hydrogen or $C_1$–$C_4$alkyl; or $R_{37}$ and $R_{38}$, together with the carbon atom to which they are attached form a 3- to 7-membered ring which may contain one or two oxygen atoms or a group NR$_{35}$ in which R$_{35}$ is hydrogen, $C_1$–$C_4$alkyl or $C_1$–$C_4$alkylcarbonyl;

$R_{39}$, $R_{40}$, $R_{41}$ and $R_{42}$ independently of one another are hydrogen or $C_1$–$C_4$alkyl, or $R_{39}$ and $R_{40}$ or $R_{41}$ and $R_{42}$, together with the carbon atom to which they are attached, form a 3- to 7-membered ring which may contain one or two oxygen atoms or a group $NR_{43}$ in which $R_{43}$ is hydrogen or $C_1C_4$ alkyl;

Z is the group

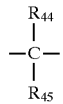

or the group

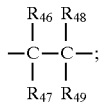

$R_{44}$, $R_{45}$, $R_{46}$, $R_{47}$, $R_{48}$ and $R_{49}$ independently of one another are hydrogen or methyl; and p is 0 or 1.

26. A process according to claim 25, wherein in the compound of the formula Ia r is 1 or 2 and $R_2$ is hydrogen, halogen, $C_1$–$C_6$ alkyl, $C_1$–$C_6$ alkoxy, $C_1$–$C_6$ haloalkoxy or cyano.

27. A process according to claim 26, wherein in the compound of the formula Ia $R_2$ is hydrogen, halogen, methyl, difluoromethoxy, trifluoromethoxy or cyano.

28. A process according to claim 25, wherein in the formula Ia p is 1 and $Y_1$ and $Y_2$ are oxygen.

29. A process according to claim 28, wherein in the formula Ia Z is the group

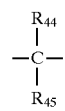

30. A process according to claim 29, wherein $R_{44}$ and $R_{45}$ are methyl.

31. A process according to claim 25, wherein the aromatic nitro compound corresponds to the formula Ib

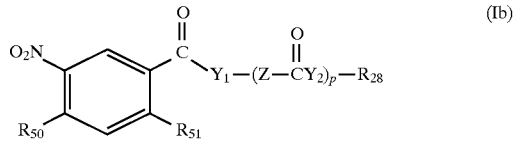

in which $Y_1$, $Y_2$, Z, p and $R_{28}$ are as defined under formula Ia in claim 19 and $R_{50}$ is hydrogen or halogen; and $R_{51}$ is hydrogen, halogen, methyl, difluoromethoxy, trifluoromethoxy or cyano.

32. A process according to claim 31, wherein in the formula Ib $R_{50}$ is hydrogen, $R_{51}$ is chlorine and $R_{28}$ is allyl.

33. A catalytic composition comprising platinum modified by a metal selected from the group consisting of lead, mercury, bismuth, germanium, cadmium, arsenic, antimony, silver and gold, which contains as promoter a compound selected from the group of iron, manganese, cobalt, copper, and ruthenium.

* * * * *

UNITED STATES PATENT AND TRADEMARK OFFICE
CERTIFICATE OF CORRECTION

PATENT NO. : 5,856,578
DATED : January 5, 1999
INVENTOR(S) : SIEGRIST ET AL.

It is certified that error appears in the above-identified patent and that said Letters Patent is hereby corrected as shown below:

Title page, left column, section [73] should read:

-- [73] Assignee: Novartis Corporation, Summit, N.J. --

Signed and Sealed this

Thirty-first Day of October, 2000

Attest:

Q. TODD DICKINSON

*Attesting Officer*　　　　*Director of Patents and Trademarks*